United States Patent [19]

Bauer et al.

[11] Patent Number: 4,863,304
[45] Date of Patent: Sep. 5, 1989

[54] RAPID CONNECTOR BETWEEN AN ENDOSCOPE AND A CAMERA

[75] Inventors: Siegfried Bauer, Heidelsheim; Helmut Lehmann, Kraichtal-Menzingen, both of Fed. Rep. of Germany

[73] Assignee: Richard Wolf, GmbH, Fed. Rep. of Germany

[21] Appl. No.: 234,631

[22] Filed: Aug. 22, 1988

[30] Foreign Application Priority Data

Aug. 22, 1987 [DE] Fed. Rep. of Germany ....... 8711421

[51] Int. Cl.⁴ ................................................ A61B 1/00
[52] U.S. Cl. ........................................ 403/37; 403/34; 354/62; 128/4
[58] Field of Search ...................... 354/62; 403/36, 37; 350/253, 582–590, 61, 63; 128/4, 6, 8, 3, 5

[56] References Cited

U.S. PATENT DOCUMENTS 4,182,558 1/1980 Matsuo ........................... 403/316 X
4,281,646 8/1918 Kinoshita ........................... 350/584
4,497,550 2/1985 Ouchi et al. ........................ 350/584

FOREIGN PATENT DOCUMENTS 7918414 6/1979 Fed. Rep. of Germany .
2279369 2/1976 France ..................... 128/6

Primary Examiner—Andrew V. Kundrat
Assistant Examiner—Franco S. Deliguori
Attorney, Agent, or Firm—Hill, Van Santen, Steadman & Simpson

[57] ABSTRACT

A rapid connector for use between an endoscope and a camera in which a base ring is connectible to a lens mount of the camera and to an ocular cone of the endoscope and comprises a delimiting glass pane with there being an enclosed space between the delimiting glass pane and a glass pane of the endoscope, and in which the enclosed space is placed in communication with a compressed air source via a radial bore in the base ring and a connector tube therein, and with the ambient atmosphere via an oppositely situated radial bore as well as a hole of the base ring.

2 Claims, 1 Drawing Sheet

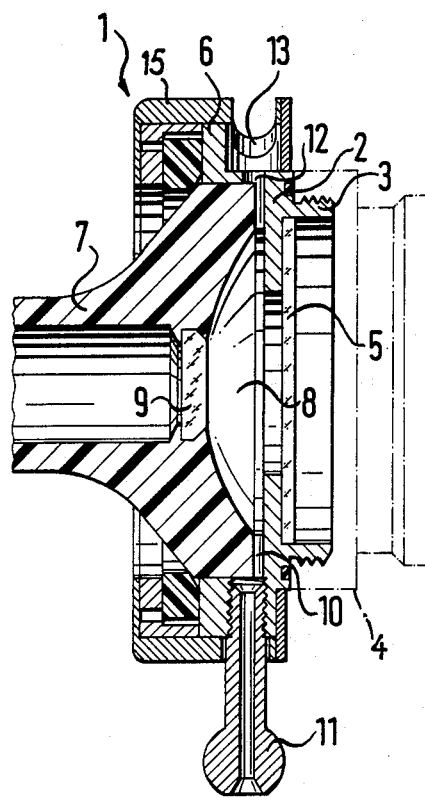

RAPID CONNECTOR BETWEEN AN ENDOSCOPE AND A CAMERA

BACKGROUND OF THE INVENTION

1. Field of the Invention

This invention relates to a rapid connector between an endoscope and a camera, of the kind in which a base ring is connectible to the lens mount of the camera and to the ocular cone of the endoscope and comprises a delimiting glass pane, with there being an enclosed space between said glass pane and a glass pane of the ocular cone of the endoscope.

2. Description of the Prior Art

Rapid connectors of this kind are described in the DE- GM 79 18 414 and are commonly produced from a light metal of high thermal conductivity. If the two parts which are to be connected, namely the endoscope and the camera are at different temperatures, humidity may give rise to condensation in the enclosed space between the glass pane of the ocular cone of the endoscope and the glass pane in the base ring because of the temperature differences. This leads to misting up of the glass panes and thereby to poor camera exposure. Residual fluid may also be present in the cone of the ocular after a disinfecting action, which also precipitates on the glass pane. This misting requires a separation of the camera from the endoscope for elimination or rather for cleaning, which results in considerable interference in the endoscopic intervention and also supplemental discomfort of the patient.

SUMMARY OF THE INVENTION

The main object of the present invention is to prevent separation between the camera and the endoscope for the purpose of removal of condensation or humidity from the space between the glass pane delimiting the ocular cone of the endoscope and the glass pane of the base ring.

To this end the present invention consists in a rapid connector for use between an endoscope and a camera in which a base ring is connectible to a lens mount of the camera and to an ocular cone of the endoscope and comprises a delimiting glass pane with there being an enclosed space between said delimiting glass pane and a glass pane of the endoscope, and in which the enclosed space is placed in communication with a compressed air source via a radial bore in the base ring and a connector tube therein, and with the ambient atmosphere via an oppositely situated radial bore as well as a hole of the base ring.

A bellows or an air pump or small pneumatic compressor may be utilized as an air source, by means of which air is blown through the space between the glass panes, whereby any possible condensate or possible residual fluid is removed rapidly and effectively.

BRIEF DESCRIPTION OF THE DRAWINGS

In order that the invention may be more readily understood, an embodiment thereof will now be described, by way of example, with reference to the accompanying drawing which is an axial cross-section of a rapid connector between an endoscope and a camera.

DESCRIPTION OF THE PREFERRED EMBODIMENT

In the following description, reference will only be made to those parts of the rapid connector which relate to or are needed to understand the invention. Those specific constructional details of the rapid connector can be obtained from the specification of DE-GM 79 18 414, the subject matter of which is incorporated into this specification by reference. Referring to the drawing, there is shown a rapid connector 1 which comprises a base ring 2 which has an annular flange 3 screwed into the mount 4 of a camera (not shown). The base ring 2 is delimited by a glass pane 5 and is connected rapidly and in an easily releasable known manner to the ocular cone 7 of an endoscope by means of a flange 6 comprising part-spherical detents or the like, and a twistable outer ring 15.

The space 8 between the glass pane 5 and the glass pane 9 of the endoscope covering the ocular, is connected to a compressed air source, e.g. a bellows, via a radial bore or passage 10 in the base ring 2 and the bore 10 has a connector tube 11 threaded therein. The space 8 is also provided with a radial bore or passage 12 located opposite the bore 10 and with a hole 13 in the outer ring 15, so that any possible condensate present in the space 8 or possible humidity therein may be blown out by means of air flowing through the space 8 by the operation of the bellows, and out of the space rapidly and effectively.

It should be appreciated that the invention is not limited to the embodiment herein described but includes all modifications and variations falling within its scope.

What is claimed is:

1. In a rapid connector for use between an endoscope and a camera, said connector having a base ring connectible to a lens mount of the camera and releasably connectible to an ocular cone of the endoscope, said base ring comprising a delimiting glass pane with means defining an enclosed space between said glass pane and a glass pane delimiting the ocular cone of the endoscope, the improvement comprising means for connecting the enclosed space with a compressed air source, including means defining a first radial passage in the base ring and a connector tube in communication with said first radial passage, and means for connecting the enclosed space with the ambient atmosphere including means defining a second radial passage in said base ring, which is opposite said first radial passage.

2. In a rapid connector according to claim 1, wherein said base ring has an outer ring thereon, said outer ring has a hole in communication with the second radial passage.

* * * * *